United States Patent
Ohman et al.

(10) Patent No.: US 11,124,539 B2
(45) Date of Patent: Sep. 21, 2021

(54) CHROMATOGRAPHY RESIN, PRODUCTION AND USE THEREOF

(71) Applicant: Cytiva BioProcess R&D AB, Uppsala (SE)

(72) Inventors: Johan William Ohman, Uppsala (SE); Mats Ander, Uppsala (SE); Therese Graner, Uppsala (SE); Anneli Jorsback, Uppsala (SE); Jinyu Zou, Uppsala (SE)

(73) Assignee: Cytiva BioProcess R&D AB, Uppsala (SE)

( * ) Notice: Subject to any disclaimer, the term of this patent is extended or adjusted under 35 U.S.C. 154(b) by 76 days.

(21) Appl. No.: 16/348,534

(22) PCT Filed: Nov. 14, 2017

(86) PCT No.: PCT/EP2017/079101
§ 371 (c)(1),
(2) Date: May 9, 2019

(87) PCT Pub. No.: WO2018/091424
PCT Pub. Date: May 24, 2018

(65) Prior Publication Data
US 2019/0263856 A1    Aug. 29, 2019

(30) Foreign Application Priority Data
Nov. 16, 2016 (GB) ..................... 1619356

(51) Int. Cl.
*C07K 1/22* (2006.01)
*B01J 20/32* (2006.01)
*B01D 15/38* (2006.01)
*B01J 20/24* (2006.01)
*B01J 20/285* (2006.01)
*B01J 20/286* (2006.01)

(52) U.S. Cl.
CPC ............ *C07K 1/22* (2013.01); *B01D 15/3828* (2013.01); *B01J 20/24* (2013.01); *B01J 20/285* (2013.01); *B01J 20/286* (2013.01); *B01J 20/321* (2013.01); *B01J 20/3212* (2013.01); *B01J 20/3217* (2013.01); *B01J 20/3274* (2013.01); *B01J 2220/52* (2013.01); *C07K 2319/20* (2013.01); *C07K 2319/92* (2013.01); *C07K 2319/95* (2013.01)

(58) Field of Classification Search
None
See application file for complete search history.

(56) References Cited

U.S. PATENT DOCUMENTS 8,114,611 B2 *  2/2012  Bian ................... C07K 14/315
                                                        435/7.1
10,087,213 B2 * 10/2018  Chen ...................... C07K 1/32
2016/0207965 A1  7/2016  Wood et al.

FOREIGN PATENT DOCUMENTS

CN     101884910 A    11/2010
WO     2014/110393 A1  7/2014

OTHER PUBLICATIONS

Bayrhuber et al. (Production of recombinant Conkunitzin-S1 in *Escherichia coli*, Protein Expression and Purification 47 (2006) 640-644). (Year: 2006).*
Singh et al. (Solubilization and Refolding of Bacterial Inclusion Body Proteins, Journal of Bioscience and Bioengineering, vol. 99, No. 4, 303-310, 2005) (Year: 2005).*
PCT International Search Report and Written Opinion for PCT Application No. PCT/EP2017/079101 dated Apr. 13, 2018 (17 pages).
Great Britain Search Report for GB Application No. 1619356.7 dated Jun. 20, 2017 (4 pages).
Guan et al., "Split Intein Mediated Ultra-Rapid Purification of Tagless Protein (SIRP)," Biotechnology and Bioengineering, 2013, 110(9):2471-2481.
Lu et al., "Split Intein Facilitated Tag Affinity Purification for Recombinant Proteins with Controllable Tag Removal by Inducible Auto-Cleavage," Journal of Chromatography A, 2011, 1218:2553-2560.
Muir et al., "Expressed Protein Ligation: A General Method for Protein Engineering," Proc. Nat. Acad. Sci. USA, 1998, 95:6705-6710.
European Office Action for EP Application No. 1780490.5 dated Aug. 24, 2020 (15 pages).

* cited by examiner

*Primary Examiner* — Suzanne M Noakes
*Assistant Examiner* — Jae W Lee
(74) *Attorney, Agent, or Firm* — Eversheds Sutherland (US) LLP (57) ABSTRACT

The present invention relates to the field of chromatography and more specifically to producing protein affinity chromatography resins comprising affinity ligands based on a N-terminal fragment of a split intein, such as DnaE from *Nostoc punctiforme*, as well as methods for using the same. The N-terminal fragments are produced in inclusion bodies in bacterial cells.

11 Claims, 3 Drawing Sheets
Specification includes a Sequence Listing.

SEQUENCE LISTING

```
<160> NUMBER OF SEQ ID NOS: 6

<210> SEQ ID NO 1
<211> LENGTH: 186
<212> TYPE: PRT
<213> ORGANISM: Artificial
<220> FEATURE:
<223> OTHER INFORMATION: Npu DnaE N-terminal intein fragment

<400> SEQUENCE: 1

Met Gly Thr Ala Leu Ser Tyr Glu Thr Glu Ile Leu Thr Val Glu Tyr
1               5                   10                  15

Gly Leu Leu Pro Ile Gly Lys Ile Val Glu Lys Arg Ile Glu Cys Thr
            20                  25                  30
```

Val Tyr Ser Val Asp Asn Asn Gly Asn Ile Tyr Thr Gln Pro Val Ala
            35                  40                  45

Gln Trp His Asp Arg Gly Glu Gln Glu Val Phe Glu Tyr Cys Leu Glu
 50                  55                  60

Asp Gly Ser Leu Ile Arg Ala Thr Lys Asp His Lys Phe Met Thr Val
 65                  70                  75                  80

Asp Gly Gln Met Leu Pro Ile Asp Glu Ile Phe Glu Arg Glu Leu Asp
                 85                  90                  95

Leu Met Arg Val Asp Asn Leu Pro Asn Lys Leu Gly Gly Gly Gly Ser
             100                 105                 110

Gly Gly Gly Gly Ser Ala Ser Met Lys Ile Glu Glu Gly Lys Leu Thr
             115                 120                 125

Asn Pro Gly Val Ser Ala Trp Gln Val Asn Thr Ala Tyr Thr Ala Gly
         130                 135                 140

Gln Leu Val Thr Tyr Asn Gly Lys Thr Tyr Lys Cys Leu Gln Pro His
145                 150                 155                 160

Thr Ser Leu Ala Gly Trp Glu Pro Ser Asn Val Pro Ala Leu Trp Gln
                 165                 170                 175

Leu Gln Leu Glu His His His His His His
            180                 185

<210> SEQ ID NO 2
<211> LENGTH: 121
<212> TYPE: PRT
<213> ORGANISM: Artificial
<220> FEATURE:
<223> OTHER INFORMATION: Npu DnaE N-terminal intein fragment

<400> SEQUENCE: 2

Met Gly Thr Ala Leu Ser Tyr Glu Thr Glu Ile Leu Thr Val Glu Tyr
 1               5                  10                  15

Gly Leu Leu Pro Ile Gly Lys Ile Val Glu Lys Arg Ile Glu Cys Thr
             20                  25                  30

Val Tyr Ser Val Asp Asn Asn Gly Asn Ile Tyr Thr Gln Pro Val Ala
            35                  40                  45

Gln Trp His Asp Arg Gly Glu Gln Glu Val Phe Glu Tyr Cys Leu Glu
 50                  55                  60

Asp Gly Ser Leu Ile Arg Ala Thr Lys Asp His Lys Phe Met Thr Val
 65                  70                  75                  80

Asp Gly Gln Met Leu Pro Ile Asp Glu Ile Phe Glu Arg Glu Leu Asp
                 85                  90                  95

Leu Met Arg Val Asp Asn Leu Pro Asn Gly Gly Gly Ser Gly Gly
             100                 105                 110

Gly Gly Ser His His His His His His
         115                 120

<210> SEQ ID NO 3
<211> LENGTH: 121
<212> TYPE: PRT
<213> ORGANISM: Artificial
<220> FEATURE:
<223> OTHER INFORMATION: Npu DnaE N-terminal intein fragment

<400> SEQUENCE: 3

Met Gly Thr Ala Leu Ser Tyr Glu Thr Glu Ile Leu Thr Val Glu Tyr
 1               5                  10                  15

Gly Leu Leu Pro Ile Gly Lys Ile Val Glu Lys Arg Ile Glu Ser Thr
             20                  25                  30

```
Val Tyr Ser Val Asp Asn Asn Gly Asn Ile Tyr Thr Gln Pro Val Ala
            35                  40                  45

Gln Trp His Asp Arg Gly Glu Gln Glu Val Phe Glu Tyr Ser Leu Glu
 50                  55                  60

Asp Gly Ser Leu Ile Arg Ala Thr Lys Asp His Lys Phe Met Thr Val
 65                  70                  75                  80

Asp Gly Gln Met Leu Pro Ile Asp Glu Ile Phe Glu Arg Glu Leu Asp
                 85                  90                  95

Leu Met Arg Val Asp Asn Leu Pro Asn Gly Gly Gly Ser Gly Gly
                100                 105                 110

Gly Gly Ser His His His His His His
            115                 120

<210> SEQ ID NO 4
<211> LENGTH: 122
<212> TYPE: PRT
<213> ORGANISM: Artificial
<220> FEATURE:
<223> OTHER INFORMATION: Npu DnaE N-terminal intein fragment

<400> SEQUENCE: 4

Met Gly Thr Ala Leu Ser Tyr Glu Thr Glu Ile Leu Thr Val Glu Tyr
 1               5                  10                  15

Gly Leu Leu Pro Ile Gly Lys Ile Val Glu Lys Arg Ile Glu Ser Thr
                20                  25                  30

Val Tyr Ser Val Asp Asn Asn Gly Asn Ile Tyr Thr Gln Pro Val Ala
            35                  40                  45

Gln Trp His Asp Arg Gly Glu Gln Glu Val Phe Glu Tyr Ser Leu Glu
 50                  55                  60

Asp Gly Ser Leu Ile Arg Ala Thr Lys Asp His Lys Phe Met Thr Val
 65                  70                  75                  80

Asp Gly Gln Met Leu Pro Ile Asp Glu Ile Phe Glu Arg Glu Leu Asp
                 85                  90                  95

Leu Met Arg Val Asp Asn Leu Pro Asn Gly Gly Gly Ser Gly Gly
                100                 105                 110

Gly Gly Ser His His His His His His Cys
            115                 120

<210> SEQ ID NO 5
<211> LENGTH: 116
<212> TYPE: PRT
<213> ORGANISM: Artificial
<220> FEATURE:
<223> OTHER INFORMATION: Npu DnaE N-terminal intein fragment

<400> SEQUENCE: 5

Met Gly Thr Ala Leu Ser Tyr Glu Thr Glu Ile Leu Thr Val Glu Tyr
 1               5                  10                  15

Gly Leu Leu Pro Ile Gly Lys Ile Val Glu Lys Arg Ile Glu Ser Thr
                20                  25                  30

Val Tyr Ser Val Asp Asn Asn Gly Asn Ile Tyr Thr Gln Pro Val Ala
            35                  40                  45

Gln Trp His Asp Arg Gly Glu Gln Glu Val Phe Glu Tyr Ser Leu Glu
 50                  55                  60

Asp Gly Ser Leu Ile Arg Ala Thr Lys Asp His Lys Phe Met Thr Val
 65                  70                  75                  80

Asp Gly Gln Met Leu Pro Ile Asp Glu Ile Phe Glu Arg Glu Leu Asp
```

85                  90                  95

Leu Met Arg Val Asp Asn Leu Pro Asn Gly Gly Gly Ser Gly Gly
                100                 105                 110

Gly Gly Ser Cys
        115

<210> SEQ ID NO 6
<211> LENGTH: 283
<212> TYPE: PRT
<213> ORGANISM: Artificial
<220> FEATURE:
<223> OTHER INFORMATION: Npu DnaE C-terminal intein fragment

<400> SEQUENCE: 6

Met Ile Lys Ile Ala Thr Arg Lys Tyr Leu Gly Lys Gln Asn Val Tyr
1               5                   10                  15

Gly Ile Gly Val Glu Arg Asp His Asn Phe Ala Leu Lys Asn Gly Phe
                20                  25                  30

Ile Ala Ser Asn Cys Phe Asn Val Ser Lys Gly Glu Glu Leu Phe Thr
            35                  40                  45

Gly Val Val Pro Ile Leu Val Glu Leu Asp Gly Asp Val Asn Gly His
        50                  55                  60

Lys Phe Ser Val Ser Gly Glu Gly Glu Gly Asp Ala Thr Tyr Gly Lys
65                  70                  75                  80

Leu Thr Leu Lys Phe Ile Cys Thr Thr Gly Lys Leu Pro Val Pro Trp
                85                  90                  95

Pro Thr Leu Val Thr Thr Leu Thr Tyr Gly Val Gln Cys Phe Ser Arg
                100                 105                 110

Tyr Pro Asp His Met Lys Gln His Asp Phe Phe Lys Ser Ala Met Pro
            115                 120                 125

Glu Gly Tyr Val Gln Glu Arg Thr Ile Phe Phe Lys Asp Asp Gly Asn
        130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Leu Glu His His His His His His
        275                 280

CHROMATOGRAPHY RESIN, PRODUCTION AND USE THEREOF

CROSS REFERENCE TO RELATED APPLICATIONS

This application claims the priority benefit of PCT/EP2017/079101 filed on Nov. 14, 2017 which claims priority benefit of Great Britain Application No. 1619356.7, filed Nov. 16, 2016, respectively. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Apr. 19, 2019, is named 285983_1.txt and is 9,017 bytes in size.

FIELD OF THE INVENTION

The present invention relates to the field of chromatography and more specifically to producing protein affinity chromatography resins comprising affinity ligands based on a N-terminal fragment of a split intein, such as DnaE from *Nostoc punctiforme*, as well as methods for using the same.

BACKGROUND OF THE INVENTION

A number of methods are available for protein purification, e.g. chromatography, which includes a variety of techniques that exploits one or more differences between the various proteins due to their intrinsic properties. These properties are largely determined by each proteins unique amino acid sequence such as protein size, charge, hydrophobicity, biological activity or specific binding affinity. In a purification process it is often required to perform a combination of filtration and chromatography, (in one or several steps using different resin supports), to reach a sufficient purity of a target protein, (or protein of interest). Moreover, a certain purification process that leads to sufficient purity for one certain target protein may not be suitable for another different target protein. Therefore, in applications where many different proteins are needed in a pure form, the use of an affinity tag system for use in affinity chromatography is an attractive alternative. Affinity tags are usually peptides or proteins that are fused to a target protein by genetic engineering. Moreover, affinity tags have known affinity ligands so that a resulting fusion protein can be rapidly purified on a suitable affinity resin in a predictable manner, where the system preferably is stable towards proteolysis and does not contain any cysteines which otherwise could interfere with the disulphide formation within a fused target protein. It is typically desirable from the perspectives of reducing any target protein stability issues to purify proteins in as short a time as possible. Moreover, it is desirable to simplify purification processes to increase protein yields and to reduce the overall cost.

A large number of different affinity tag fusion systems have been described, for example a commonly used affinity tag is the poly-histidine tag, which includes a sequence of two or more consecutive histidine's appended on either side to a target protein amino acid sequence. Poly-histidine tag fusion proteins are usually purified by using immobilized metal ion chromatography, (IMAC), resins or filters, wherein the ligand consists of divalent metal ions such as $Ni^{2+}$-ions complexed to immobilized chelating substances. In addition to poly-histidine tags, there is a large number of examples in the literature on various smaller peptidic or larger protein-based affinity tags. Even if the purity of an affinity tagged fusion protein is sufficient with regard to other unwanted proteins or non-protein contaminants, there is a possible disadvantage with affinity tags in that they remain fused to the target protein after purification and that the affinity tag may interfere with subsequent research. An affinity tag may alter or affect the structure and function of a target protein and may also give other unwanted effects, especially if used in vivo. For certain applications it may therefore be necessary to remove the affinity tag after a purification, for example if the affinity tag causes immune responses or alter the structural or functional properties of a target protein. One solution for removal of an affinity tag from a target protein is to insert a specific amino acid recognition sequence for peptide bond cleavage between the affinity tag and the target protein by the use of certain chemical agents, enzymes or proteases. Inefficient or non-specific cleavage is however a potential drawback. Moreover, the use of chemical agents or proteases may be expensive especially in larger scale processes. Also, this method for removal of an affinity tag may require additional steps in the purification process to obtain optimal cleavage conditions and to subsequently remove the added chemicals or proteases.

An alternative approach to remove an affinity tag is by insertion of a self-cleaving enzyme between the affinity tag and the target protein. This enables the elution of a target protein from the affinity gel resin in response to an enzymatic self-cleavage event, leaving the enzyme and the affinity tag on the gel resin. Intein-based affinity tag systems can be used for purification of tag-less target proteins in a single purification step without addition of chemical agents or proteases. Inteins are enzymes that excise themselves out of larger linear protein sequences and join the flanking sequences (N-/C-exteins), in a natural process known as protein splicing. Inteins may also be used to introduce carboxy-terminal protein thioesters for use in a technology known as expressed protein ligation (Muir T W, Sondhi D, Cole P A. Proc Natl Acad Sci USA. 1998; 95:6705). Mutation of key catalytic residues of some inteins may convert these inteins into self-cleaving enzymes suitable for tag removal in protein purification (Gene 231:1-13). An advantage with the intein system is that recombinant, tag-less proteins can be purified in a single step using affinity chromatography. A disadvantage may often be the cleavage kinetics, such that to achieve sufficient levels of cleavage and thus sufficient yield of a tag-less target protein, the incubation may require 16 hours of incubation or more. Also, the enzymatic intein activity will be present already after the start of expression in host cells, which may result in unwanted premature cleavage and therefore a loss of target protein yield.

Premature cleavage of intein fusion proteins can be minimized by using so called split inteins instead. Split inteins have their catalytic residues divided between two separate protein fragments, N- and C-inteins, and are only active when the two fragments interact. A large group of naturally split inteins are the cyanobacterial DnaE inteins. A genetically engineered variant of a naturally split intein, DnaE from *Nostoc punctiforme* (NpuDnaE), wherein the N-terminal fragment is used as a ligand, and the C-terminal fragment as an affinity tag, has shown high cleavage yields even at relatively short incubation times (Biotechnol Bioeng. 2013 September; 110(9):2471-81), (WO2014/110393A1). The splicing activity in this split intein system has been inactivated by mutations to key catalytic residues and the only remaining activity is the C-terminal cleavage activity, which may explain some of the improved kinetics. This system has certain advantages such as affinity purification combined with affinity tag removal, especially in smaller scale batch processes, but has limitations for repeated usage. This split intein system relies on a second additional affinity tag fused to the ligand for immobilization to a chromatography resin support. In this system there is a potential risk for ligand leakage during the purification process and especially during cleaning and restoring of the resin support for repeated usage using harsh conditions. Such ligand leakage is undesirable from a purification perspective, since the binding capacity of the resin support may be affected as well as the final purity of the isolated target protein. Moreover, a standard process for cleaning and restoring of a chromatography resin under acidic or alkaline conditions, (cleaning-in-place or CIP), for repeated usage s is typically preferred for protein purification processes.

In the prior art system described in WO2014/110393A1, both the affinity ligand and the affinity tagged target protein have to be produced for use in this system, so the split intein system is currently similar to a two-step procedure. Moreover, the highly exposed hydrophobic surface of the intein N-fragment of DnaE tends to interfere with the folding and/or solubility during expression, potentially causing aggregation and loss of yield, thus limiting the use of this split intein system. One strategy for the production of recombinant split intein DnaE N-fragment includes appending an affinity tag to increase the solubility of the resulting fusion protein and to facilitate the subsequent purification. Another strategy for increased production of soluble recombinant DnaE N-fragment is to reduce the temperature of a bacterial cell culture after inducing expression from a higher initial temperature e.g. 30-37° C. to a lower temperature during expression at about 18-25° C. However, overall expression yields are generally less at lower temperatures. Therefore, there is a need both for an improved production method for the split intein ligand to get higher yields and also for an improved resin support which can be reused several times even after harsh cleaning procedures. An improved affinity resin would allow predictable purifications, preferably in formats such as columns or filters for use together with chromatography systems for increased versatility and efficiency.

SUMMARY OF THE INVENTION

The present invention provides an improved chromatography resin with immobilized/attached N-terminal intein fragments which provides higher ligand densities and enables multiple re-use even after harsh cleaning procedures.

In a first aspect, the invention relates to a method for production of an affinity chromatography resin comprising an amino-terminal, (N-terminal), split intein fragment as an affinity ligand, comprising the following steps:
a) expression of an N-terminal split intein fragment protein, preferably comprising a sequence selected from SEQ ID NO:s 1-5, as insoluble protein in inclusion bodies in bacterial cells, preferably *Escherichia coli*, (*E. coli*),
b) harvesting said inclusion bodies;
c) solubilizing said inclusion bodies and releasing expressed protein;
d) binding said protein on a solid support;
e) refolding said protein;
f) releasing said protein from the solid support; and
g) immobilizing said protein as ligands on a chromatography resin to form an affinity chromatography resin.

Refolding is preferably done with the protein bound to the solid support but may also be done after releasing the protein from the solid support. The solid support in step d) may be any solid support providing interaction with the expressed protein, such as an ion exchange or IMAC solid support.

Preferably the chromatography resin is selected from agarose, polystyrene, methacrylate or cellulose beads, most preferably agarose beads. According to a preferred embodiment the immobilization in step g) is by covalent attachment.

In one embodiment the immobilization is preceded by concentration, for example by ultra-filtration or other suitable concentration techniques, to a protein concentration between 5-30 mg/ml.

According to the invention the ligand density on said chromatography resin is 2-10 mg ligand/ml resin, preferably ≥3 mg ligand/ml resin, most preferably ≥5 mg ligand/ml resin.

The chromatography resin is preferably packed in columns or used in fluidized beds, porous monoliths, capillary beds, magnetic beads or other formats, such as batch format, where the target protein can be captured and mobile buffers can be changed.

Besides chromatography resins it is also possible to use for example capture filtration and filter beds.

In one embodiment of the above method, the N-terminal fragments are poly-histidine tagged and selected from SEQ ID NO:s 1-4 and the soluble protein is purified by IMAC chromatography. In another embodiment of the above method, the N-terminal fragment is SEQ ID NO 5 and the soluble protein is purified by ion exchange (IEX) chromatography.

In a second aspect, the invention relates to recombinant proteins or ligands according to SEQ ID NO: 1-5. The proteins/ligands may be immobilized to any type of solid support, such as a surface, particle or bead.

In a third aspect, the invention relates to an affinity chromatography resin, wherein N-terminal split intein fragments according to SEQ ID NO:s 1-5, or sequences having at least 95% homology therewith, have been covalently attached to the resin in a ligand density of 2-10 mg/ml.

Preferably the resin comprises porous beads, preferably agarose beads. The agarose beads are preferably epoxy-activated but may also be N-hydroxysuccinimide or cyanobromide-activated.

In a fourth aspect the invention relates to a method of using or use of the chromatography resin described above for protein purification, comprising capture of recombinant NpuDnaE C-fragment tagged target proteins on said affinity resin provided with recombinant NpuDnaE N-fragment ligands, followed by changing the conditions to promote the release of tag-less target protein into a liquid eluent whereas the NpuDnaE C-fragment tag and the NpuDnaE N-fragment ligand remain complexed and bound to said chromatography resin.

An advantage of the chromatography resin is that it may be re-used several times after cleaning using harsh conditions, such as 0.05-0.5 M NaOH.

Expression of the ligands (SEQ ID NO:2 1-5) and the tag (SEQ ID NO 6) is described below and conversion of the amino acids sequences into corresponding nucleic acids sequences is well known for a person skilled in the art.

The invention is useful for purification of all types of proteins, especially therapeutic proteins with high demands on being free from tags used during production thereof.

BRIEF DESCRIPTION OF SEQUENCE LISTING

A Sequence listing is enclosed at the end of the description. Here is a short summary of the sequences.

SEQ ID NO 1: Npu DnaE N-terminal intein fragment with mutation C4A at N-terminus and chitin binding domain (CBD) and polyhistidine (His6) affinity tags at C-terminus.

SEQ ID NO 2: Npu DnaE N-terminal intein fragment with mutation C4A at N-terminus and polyhistidine (His6) affinity tag at C-terminus.

SEQ ID NO 3: Npu DnaE N-terminal intein fragment with mutations C4A, C31S, C62S and polyhistidine (His6) affinity tag at C-terminus.

SEQ ID NO 4: Npu DnaE N-terminal intein fragment with mutations C4A, C31S, C62S and polyhistidine (His6) affinity tag at C-terminus. Terminal cysteine.

SEQ ID NO 5: Npu DnaE N-terminal intein fragment with mutations C4A, C31S, C62S and terminal cysteine.

SEQ ID NO 6: Npu DnaE C-terminal intein fragment with mutations D17G appended to eGFP and polyhistidine (His6) affinity tag at C-terminus.

DETAILED DESCRIPTION OF THE INVENTION

The present invention provides novel engineered N-fragments of NpuDnaE, described as SEQ ID NO:s 1-5. It was surprisingly discovered that it was possible to separately immobilize each of these fragment after refolding onto a solid support and maintain both the binding activity towards the C-fragment of the split intein, as exemplified by SEQ ID NO: 6, and also the self-cleavage functionality that results in elution of a tag-less target protein by altering the conditions of a mobile phase during the purification process.

The present invention provides a method in which the N-terminal fragment of modified and histidine-tagged NpuDnaE split inteins according to SEQ ID NO:s 1-4, are over-expressed in bacterial cell cultures, producing mainly insoluble protein as inclusion bodies. After harvesting of the cells and expressed insoluble proteins, the cells are disrupted by chemical and/or mechanical methods. Optionally soluble components such as nucleic acid, host cell proteins and other biomolecules are removed from insoluble proteins by centrifugation. Protein denaturing excipients, such as high concentration of urea or guanidine-HCl, are added to the insoluble proteins or to the protein pellet and preferably a buffering liquid is added to promote solubilization with a pH>7. Optionally the suspension is mixed by mechanical methods. Insoluble material is then removed before contacting the solution with solubilized proteins to a column containing an immobilized metal affinity chromatography, (IMAC), resin, that has been equilibrated in a buffer containing denaturing excipients at pH>7. Thereafter a buffer with pH>7 containing a high concentration of denaturing excipients is loaded to the column. The concentration of the denaturing excipients is then decreased gradually or stepwise to no or low concentration. The modified and histidine-tagged NpuDnaE N-fragment variants are then recovered by increasing amounts of imidazole in the running buffer. Optionally, an aliphatic or aromatic disulphide excipient may be added in a sufficient excess compared with the recovered protein to block any free thiols of the cysteines in the NpuDnaE N-fragment. The salts and buffer components of the recovered protein is exchanged by dialysis or by size-exclusion chromatography into a phosphate buffer with a pH between 7-11, preferably between 8-10.

Optionally the protein solution is concentrated by ultrafiltration or other suitable concentration techniques to a concentration between 5-30 mg/ml. Protein solution is then contacted with epoxy-activated porous polymer beads at a certain temperature with the addition of salt for a certain amount of time for covalent attachment of the NpuDnaE N-fragment variants onto the beads. The beads are then washed with varying solutions to remove non-covalently linked protein.

An alternative method of the present invention is provided in which the N-terminal fragment of a modified NpuDnaE split intein according to SEQ ID NO: 5, is over-expressed in bacterial cell cultures, producing mainly insoluble protein. After harvesting of the cells and expressed insoluble proteins the cells are disrupted by chemical and/or mechanical methods. Optionally soluble components such as nucleic acid, host cell proteins and other biomolecules are removed from insoluble proteins by centrifugation. Protein denaturing excipients, such as high concentration of urea or guanidine-HCl, are added to the insoluble proteins or to the protein pellet and preferably a buffering liquid is added to promote solubilization with a pH>7. Optionally the suspension is mixed by mechanical methods. Insoluble material is then removed before contacting the solution with solubilized proteins to a column containing an ion exchange chromatography, (IEX), resin, that has been equilibrated in a low conductivity buffer containing denaturing excipients at pH>7. Thereafter a buffer with pH>7 containing a high concentration of denaturing excipients with a low conductivity is loaded to the column. The concentration of the denaturing excipients is then decreased gradually or stepwise to no or low concentration. The modified NpuDnaE N-fragment is then recovered by increasing amounts of sodium chloride in the running buffer.

Optionally, a reducing agent or alternatively an aliphatic or aromatic disulphide excipient may be added in a sufficient excess compared with the recovered protein to ensure that the cysteine thiols are either in a reduced state or alternatively in an oxidized state. The salts and buffer components of the recovered protein is exchanged by dialysis or by size-exclusion chromatography into a phosphate buffer with a pH between 7-11, preferably between 8-10.

Optionally the protein solution is concentrated by ultrafiltration or other suitable concentration techniques to a concentration between 5-30 mg/ml. The protein solution is then contacted with pre-activated porous polymer beads at a certain temperature with the addition of salt for a certain amount of time for covalent attachment of the NpuDnaE N-fragment onto the beads. The beads are then washed with varying solutions to remove non-covalently linked protein.

Although the experimental procedures described below have only involved gel resins made of agarose polymers, the invention can be extended to gel resins or chromatography matrices in any material to which a biospecific ligand is covalently attached that are suitable for affinity purification procedures. Commonly used materials include agarose, cellulose, dextran, polyacrylamide, latex, silica, polymethacrylate and polystyrene. Useful solid supports are those that have a large effective surface area and good mechanical and chemical stability. Porous beaded resins usually provides the most useful properties.

Although the experimental procedures described below only include direct immobilization techniques where an affinity ligand in certain suitable buffers are combined with a chemically activated solid phase support to enable the formation of covalent bonds between the ligand and the solid phase, an indirect method could be used to reproduce the same functionality. Thus in a further embodiment the invention relates to a method in which an affinity tag is appended to the ligand and used for a first capture onto a solid support containing a binding substance for this affinity tag, followed by subsequent cross-linking of the ligand fusion protein to the solid support.

Furthermore, the invention provides a method for purification of a tag-less target protein followed by cleaning in place, CIP, using conventional cleaning solutions. The method comprises providing a sample in a suitable mobile phase containing a fusion protein consisting of a target protein with an appended affinity tag which comprises the C-fragment of a split intein and variants thereof; combining the sample with a chromatography resin including a covalently immobilized ligand comprising an engineered variant of a split intein to effect reversible binding of the split intein fragments to form a catalytically active intein complex; changing the buffer conditions of the mobile phase to promote the catalytic cleavage event; and isolating the tag-less target protein in the mobile phase. The chromatography resin is then washed with a CIP solution, e.g. sodium hydroxide in concentrations ranging from 10-500 mM, to dissociate the remaining intein complex whereby non-covalently bound proteins such as the split intein C-fragment can be removed from the mobile phase.

EXAMPLES

The invention will now be described more closely in relation to some non-limiting examples and the accompanying drawings.

Example 1: Production and Purification of NpuDnaE N-Fragment, SEQ ID NO. 1

*E. coli* Transformation

To promote the formation of inclusion bodies, an *E. coli* expression vector pJ401 comprising a strong inducible T5 promoter, kanamycin marker and the synthetic gene insert for expression of the protein according to SEQ ID NO. 1 was used. Standard transformation with 20 ng vector (pJ401); 1 µl vector to 50 µl cells (*E. coli* BL21 (DE3)), incubate on ice for 20 min, heat-shock for 60 sec at 42° C., incubate 2 min on ice, add 450 µl Luria-Broth, (LB), incubate at 37° C. shaking for 60 min. Spread 100 µl onto LB agar-plate containing 50 µg/ml kanamycin, incubate over night at 37° C. Working cell bank, (WCB), is made with 10 ml LB-broth in Falcon-tube, supplemented with 50 µg/ml kanamycin. Incubate for about 3 h, measure OD 600 nm. At OD about 0.8, add 2 ml 85% glycerol to final conc. 14% in tubes. Freeze in −70° C. in 1 ml aliquots.

Bacterial Cell Cultivation

Distribute about 500 ml of autoclaved Terrific-Broth, (TB) into baffled shaker flasks. Add 125 µl stock kanamycin solution to each shaker flask to get a final concentration of 25 µg/ml. Add 500 µl of *E. coli* WCB to each shaker flask. Incubate in incubator shaker at 37° C. at 180 rpm for about 5-6 hours until OD 600 increases to 1.0. Add 0.3 ml 1 M Isopropyl β-D-1-thiogalactopyranoside, (IPTG), to each shaker flask to start protein expression and maintain the temperature at 37° C. to further promote formation of inclusion bodies. Harvest the cells after 3-4 hours by centrifugation for 15 min, (2000×g in Beckman-Coulter Avanti J-26XP centrifuge with JS-4.0 rotor). Remove supernatant and weigh the wet cell pellet.

Solubilization and Refolding of NpuDnaE N-Fragment

Pellet was resuspended with 4 ml 1% Triton X-100 per gram wet-weight. The pellet was homogenized, (IKA T10 ULTRA-TURRAX) and centrifuged at 58000×g (rotor JA-25.5) for 15 minutes. The supernatants were discarded. Pellet was resuspended with 4 ml 0.8% Triton X-100, 0.5 M NaCl per gram wet-weight. The pellet was homogenized and centrifuged at 58000×g (rotor JA-25.5) for 15 minutes. The supernatant was discarded. The insoluble protein pellet was resuspended and solubilized with ~0.3 ml solubilization buffer, (100 mM sodium phosphate, 8 M urea, pH 7.4), per gram protein pellet. A reducing agent, TCEP, (tris(2-carboxyethyl)phosphine), was added to final concentration 15 mM. The protein solution was incubated with end-over-end rotation for about 30 minutes and then centrifuged at 58000×g (rotor JA-25.5) for 20 minutes. 2 ml of the supernatant was applied to two serially connected 5 ml HisTrap HP columns, (GE Healthcare) previously equilibrated with solubilization buffer at 2 ml/min. The columns were washed with 50 ml solubilization buffer followed by a linear gradient from 8 M to 0.9 M urea in 100 mM sodium phosphate buffer pH 7.4 in a total volume of 100 ml at 0.5 ml/min. The columns were further washed with 50 ml 100 mM sodium phosphate buffer, 0.9 M urea, pH 7.4 supplemented with 10 mM imidazole at 5 ml/min. Bound protein was eluted and isolated with a linear gradient from 10-500 mM imidazole in 100 mM sodium phosphate buffer, 0.9 M urea, pH 7.4 in a total volume of 50 ml at 5 ml/min. The final yield was about 2.6 mg protein per g wet-weight of initial cell pellet.

Cleavage Analysis with Purified NpuDnaE N-Fragment

Eluted protein from pooled IMAC fractions was reduced with dithiothreitol and then applied to a HiPrep 26/10 Desalting column, (GE Healthcare), equilibrated with 100 mM sodium phosphate, 1 mM EDTA, pH 8.0 for buffer exchange. The total amount of protein in the purified pool was determined by absorbance measurements to about 15 mg according to the Beer-Lambert law using the theoretical absorbance coefficient based on the amino acid sequence, (Abs 0.1% (=1 g/l): 1.656). Cleavage activity was tested by mixing 30 µl (20 µg) pure NpuDnaE N-fragment with 30 µl (30 µg) of a pure test protein, (C-GFP, i.e. GFP tagged with C-terminal fragment according to SEQ ID no. 6) in 40 µl of cleavage buffer, (50 mM Tris, 150 mM NaCl, 1 mM TCEP, 5 mM EDTA pH 7.7) at ambient temperature. The test was stopped after 60 minutes by adding SDS sample buffer to each sample and heating for 3 minutes at 95° C. SDS-PAGE was carried out on Amersham WB system, (GE Healthcare), using gel card 14, 13.5% with Cy-5 labelling.

Figure 1:
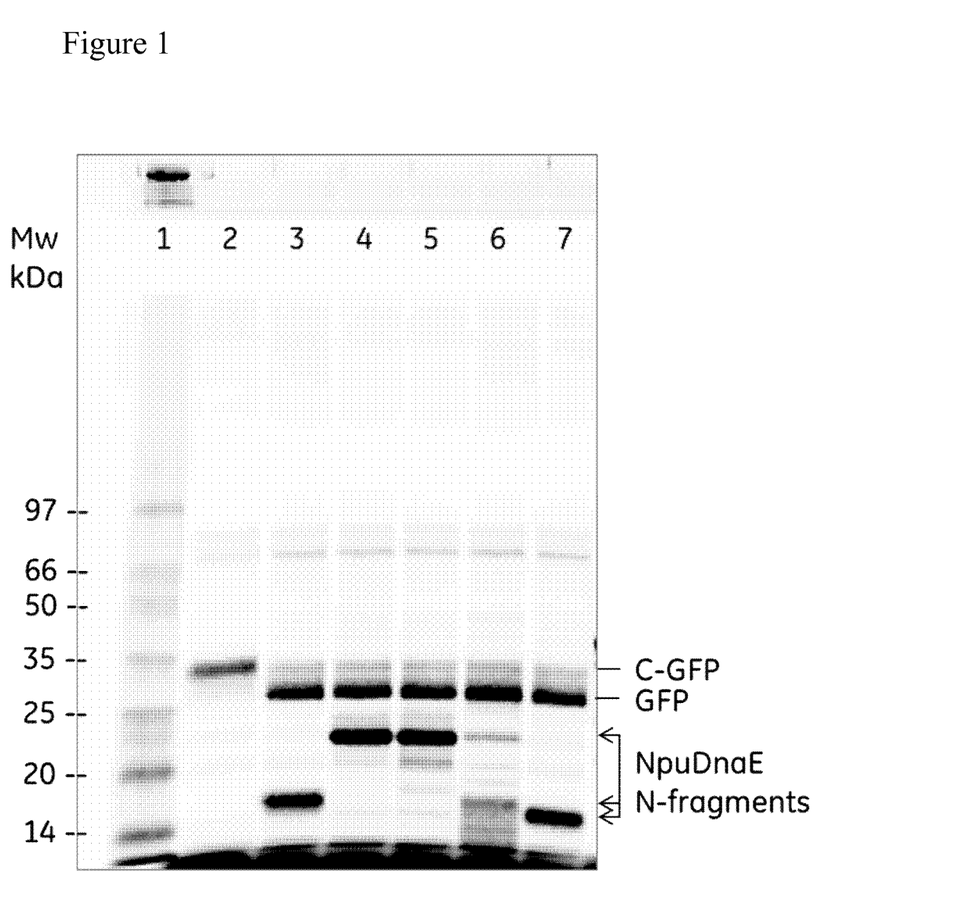
FIG. 1: SDS-PAGE showing the results after an activity test in solution where purified ligand prototypes of the invention are mixed with a purified test protein and incubated for 60 minutes.

FIG. 1 shows the SDS-PAGE with the protein pattern from a molecular size marker (lane 1) and the pure intact test protein C-GFP, (NpuDnaE C-fragment in fusion with Green Fluorescent Protein, SEQ ID no. 6) in lane 2. Lanes 3-7 show protein patterns from various different purified NpuDnaE N-fragment variants after mix with the test protein in solution. Cleavage was observed in all tested mixed samples by a decrease of about 4 kDa in size of the test protein C-GFP, corresponding to the size of the NpuDnaE C-fragment. Ligands used in cleavage samples shown in lanes 3 (SEQ ID no. 3), 4 (SEQ ID no. 1) and 7 (SEQ ID no. 5) were produced from the insoluble pellets after centrifugation of bacterial cell extracts according to either Example 1 or 2. Ligands in lanes 5 (SEQ ID no. 1) and 6 (SEQ ID no. 2) were purified from the supernatants after centrifugation of bacterial cell extracts in non-denaturing buffers.

Example 2: Production and Purification of NpuDnaE N-Fragment, SEQ ID NO: 5

*E. coli* Transformation

To promote the formation of inclusion bodies, an *E. coli* expression vector pJ401 comprising a strong inducible T5 promoter, kanamycin marker and the synthetic gene insert for expression of the protein according to SEQ ID no. 5 was used. Standard transformation with 20 ng vector (pJ401), 1 μl vector to 50 μl cells (*E. coli* BL21 (DE3)), incubate on ice for 20 min, heat-shock for 60 sec at 42° C., incubate 2 min on ice, add 450 μl LB medium, incubate at 37° C. shaking for 60 min. Spread 100 μl onto LB agar-plate containing 50 μl/ml kanamycin, incubate over night at 37° C. WCB is made with 10 ml LB-broth in falcon-tube, supplemented with 50 μg/ml kanamycin. Incubate for about 3 h, measure OD 600 nm. At OD about 0.8, add 2 ml 85% glycerol, final conc. 14% in tubes. Freeze in −70° C. in 1 ml aliquots.

Bacterial Cell Cultivation

Distribute about 500 ml of autoclaved TB medium into baffled shaker flasks. Add 125 μl stock kanamycin solution to each shaker flask to get a final concentration of 25 μg/ml. Add 500 μl of *E. coli* WCB to each shaker flask. Incubate in incubator shaker at 37° C. at 180 rpm for about 5-6 hours until OD 600 increases to 1.0. Add 0.3 ml 1 M IPTG to each shaker flask to start protein expression and maintain the temperature at 37° C. to further promote formation of inclusion bodies. Harvest the cells after 4 hours by centrifugation for 15 min, (4000×g in Beckman-Coulter Avanti J-26XP centrifuge with JS-4.0 rotor). Remove supernatant and weigh the wet cell pellet. Store cell pellet in freezer until use.

Solubilization and Refolding of NpuDnaE N-Fragment

Frozen cells from 2 litres of initial cell culture were resuspended in 5 ml 20 mM Tris-HCl pH 8.5, 20 mg/ml DNAse per gram wet cell paste. Homogenization was done using an Emulsiflex-C3 homogenizer at 20,000 psi and 4 passages in total. The cell lysate was centrifuged for 38 minutes at 58000×g (rotor JA-25.5). Supernatants were discarded and pellets were resuspended with 4 ml 1% Triton X-100 per gram wet-weight. The pellets were homogenized, (IKA T10 ULTRA-TURRAX) and centrifuged at 58000×g (rotor JA-25.5) for 15 minutes. The supernatants were discarded. Pellets were resuspended with 4 ml 0.5% Triton X-100, 2.5 M NaCl per gram wet-weight. The pellets were homogenized and centrifuged at 58000×g (rotor JA-25.5) for 15 minutes. The supernatants were discarded. Pellets were resuspended with 4 ml 2.5 M NaCl per gram wet-weight. The pellets were homogenized and centrifuged at 58000×g (rotor JA-25.5) for 15 minutes, (this step repeated once more). Finally, pellets were resuspended with 2 ml 20 mM Tris-HCl pH 8.0 per gram wet-weight. The pellets were homogenized and centrifuged at 58000×g (rotor JA-25.5) for 15 minutes. The insoluble protein pellets were combined, resuspended and solubilized with ~3 ml solubilization buffer, (20 mM Tris-HCl, 8 M urea, 50 mM DTT, 1 mM EDTA pH 8.5), per gram protein pellet. The protein solution was incubated with end-over-end rotation for about 30 minutes and then centrifuged at 58000×g (rotor JA-25.5) for 20 minutes.

30 ml of the supernatant was applied to two serially connected 5 ml HiTrap Capto Q columns, (GE Healthcare), equilibrated with solubilization buffer, (containing less DTT at 1 mM), at 3 ml/min. The columns were washed with 80 ml solubilization buffer followed by a linear gradient from 8 M to 0.9 M urea in solubilization buffer in a total volume of 90 ml at 0.5-1.5 ml/min. The columns were further washed with 50 ml 20 mM Tris-HCl, 1 mM DTT, 1 mM EDTA, 0.9 M urea buffer pH 8.5 at 6 ml/min. Bound protein was eluted and isolated with a linear gradient from 0-1 M NaCl in wash buffer in a total volume of 50 ml at 6 ml/min. The total amount of protein in the purified pool was determined by absorbance measurements to about 87 mg according to the Beer-Lambert law using the theoretical absorbance coefficient based on the amino acid sequence, (Abs 0.1% (=1 g/l): 1.011). Eluted protein was concentrated by ultra-filtration, reduced by addition of dithiothreitol and then the buffer was changed to 100 mM sodium phosphate, 1 mM EDTA, pH 8.5 on a desalting column.

Cleavage activity was tested by mixing 30 μl (10 μg) Npu DnaE N-fragment with 30 μl (30 μg) of a test protein, (C-GFP, SEQ ID no. 6), in 40 μl of cleavage buffer, (50 mM Tris, 150 mM NaCl, 1 mM TCEP, 5 mM EDTA pH 7.7) at ambient temperature. The test was stopped after 60 minutes by adding SDS sample buffer to each sample and heating for 3 minutes at 95° C. SDS-PAGE was carried out on Amersham WB system, (GE Healthcare), using gel card 14, 13.5% with Cy-5 labelling.

FIG. 1 shows the SDS-PAGE analysis after incubation of purified C-GFP, (SEQ. ID no. 6), with various different purified NpuDnaE N-fragment constructs in solution. Refolded ligand (SEQ ID no. 5), mixed with the test protein in cleavage buffer for 60 minutes is shown in lane 7.

The pure full-length test protein is shown in lane 2 and a molecular size marker is shown in lane 1. Cleavage was observed by a decrease of about 4 kDa in size of the test protein C-GFP, corresponding to the size of the NpuDnaE C-fragment. Ligands shown in lanes 3, 4 and 7 were derived from the insoluble pellet after centrifugation of bacterial cell extracts according to examples 1 and 2. Ligands in lanes 5 and 6 were purified from the supernatants after centrifugation of bacterial cell extracts.

Example 3: Covalent Immobilization of NpuDnaE N-Fragment onto Agarose Beads

Epoxide Activation of Highly Cross-Linked Agarose Beads

Drained base matrix, 20.5 gram, was washed with 100 ml distilled water, and was then transferred to a round bottom flask. 7 ml distilled water and 3.4 gram NaOH pellets were added and mechanical propeller stirring was applied. The flask was immersed into a preheated bath. After 5 minutes 6.2 ml epichlorohydrin, (ECH), was added and the reaction was progressed for 2 hours. The gel was washed with 300 ml distilled water until pH<8.

The epoxide amount was measured with titration using sodiumthiosulphate dissolved in distilled water with initial pH set to 6.8-7.0 and was determined to 8.3 μmol/ml.

Coupling of NpuDnaE N-Fragment, SEQ ID NO. 5 to Epoxide-Activated Beads

Epoxy activated gel, 6 gram, was washed with 0.1 M sodium phosphate, 1 mM EDTA pH 8.5. To the gel, refolded and purified NpuDnaE N-fragment from SEQ ID no. 5 protein solution (4.5 ml, 16.1 mg/ml in 0.1 M sodium phosphate, 1 mM EDTA pH 8.5), was added followed by sodium sulfate, 2.1 g. The reaction solution was left with rotational stirring for 4 hours at 33-34° C. in a preheated glycerol bath. The pH was measured and remained at pH 8.2-8.3. The gel was then washed with 18 ml of 0.1 M sodium phosphate, 1 mM EDTA pH 8.5 followed by wash with 60 ml with distilled water. Deactivation of remaining epoxide groups were done by adding 6 ml of 0.1 M sodium phosphate, 1 mM EDTA, 7.5% thioglycerol at pH 8.2 to the gel and mixing at room temperature over night, (16-20 h), with rotational stirring. The gels were washed with 12 ml 20% ethanol in water. Extensive washing was then done by packing the gel into 1 ml columns and washing with 50 mM NaOH followed by wash with 1.5 M NaCl. One column was dismantled and the ligand concentration was analyzed by amino acid analysis. A 1.0 ml sample of the gel resin from the dismantled column was washed with aceton and then dried in a vacuum oven at 50° C. overnight and the dry weight of the gel resin was determined by subtracting the mass of the pre-weighed glass filter from the mass of the filter with the gel after drying. The dry weight of the prototype was 77.6 mg/ml and the amount of covalently coupled ligand was 5.3 mg/ml according to amino acid analysis or 414 µM since the size of ligand from SEQ ID no. 5 is 12.8 kDa.

Example 4: Purification of Green Fluorescent Protein, (GFP), Using NpuDnaE C-Fragment Tagged GFP and Prototype NpuDnaE N-Fragment Chromatography Resin A column was packed with 1 ml chromatography resin with immobilized ligand according to SEQ ID NO. 5, for use in a medium pressure liquid chromatography system, (ÄKTA pure, GE Healthcare). The column was equilibrated with 10 ml binding buffer, (10 mM MES, 100 mM NaCl, 0.5 mM $ZnCl_2$, pH 6.0) at 1 ml/min.

GFP was expressed with a C-terminal tag according to SEQ ID NO: 6. A cell pellet from the expression of C-GFP according to SEQ. ID NO: 6 in E. coli was resuspended with 10 ml lysis buffer, (50 mM sodium phosphate, 500 mM NaCl, pH 6), per gram cell pellet. The cells were lysed by ultrasonication, (Sonics VibraCell with micro-tip), run at 35% amplitude and cycles of 10 sec on, followed by 10 sec off during 3.5 min. The cell lysate was centrifuged for 30 minutes at 48000×g and 5° C., (Beckman centrifuge, rotor JA 25.50). The clarified supernatant was supplemented with $ZnCl_2$ from a 100 mM stock solution to get a final Zn-ion concentration of 0.5 mM. The samples were centrifuged at 10000×g for 10 minutes just prior to sample application on the equilibrated column. After application of 1 ml sample to the column at 1 ml/min, the column was washed with binding buffer to remove unbound proteins. Two ml of cleavage buffer, (10 mM MES, 100 mM NaCl, 5 mM EDTA, pH 6.0), was pumped onto the column followed by a pause for 30 minutes. The cleaved GFP was eluted in the cleavage buffer and isolated followed by pumping regeneration solution, (50 mM NaOH, 1.5 M NaCl), through the column. After regeneration, the column was once again washed with first cleavage buffer followed by binding buffer to prepare for another purification cycle.

Figure 2:
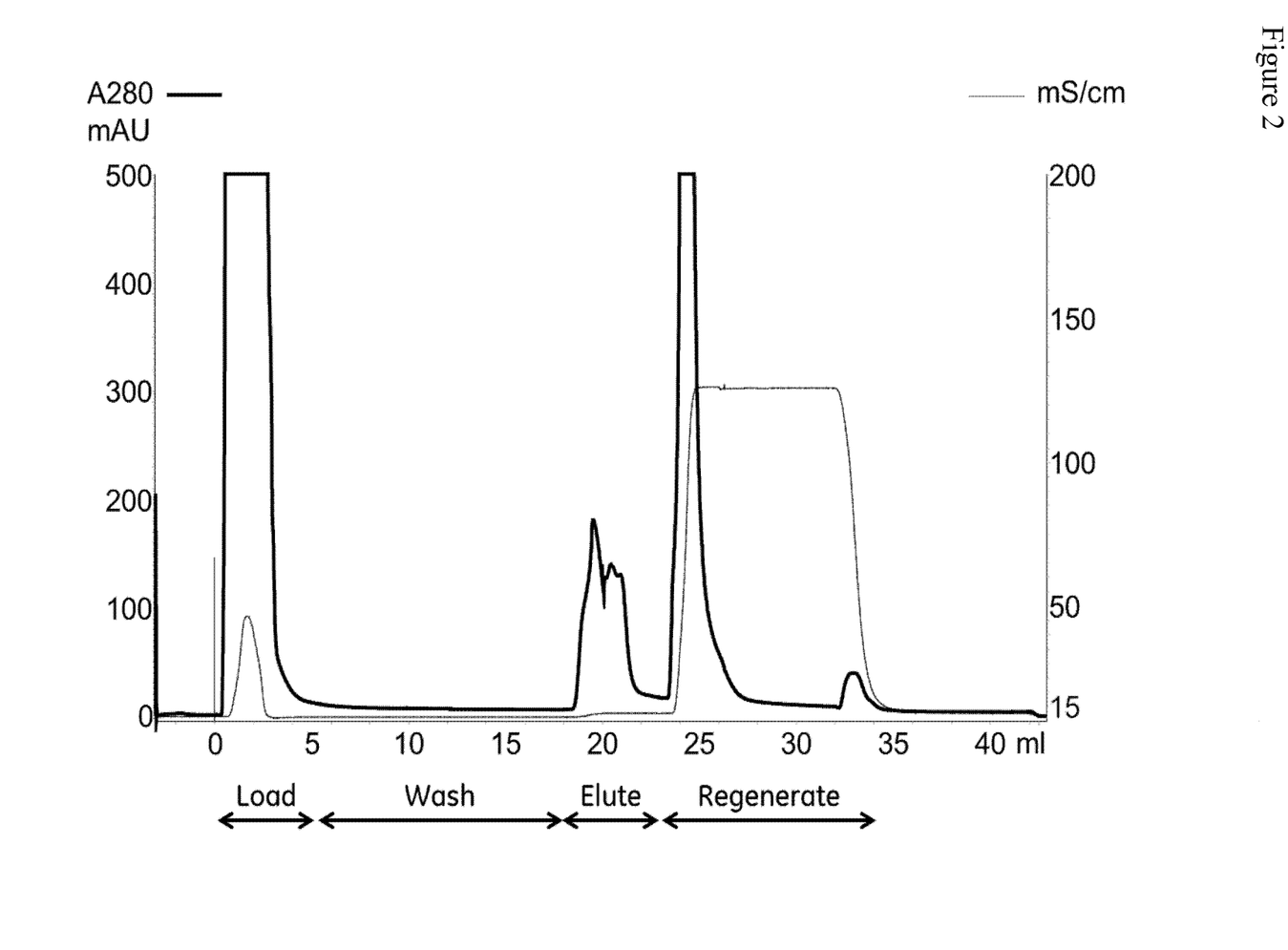
FIG. 2: Chromatogram showing purification of tag-less GFP on an affinity resin with immobilized N-intein of the invention after loading the fusion protein C-GFP.
Figure 3:
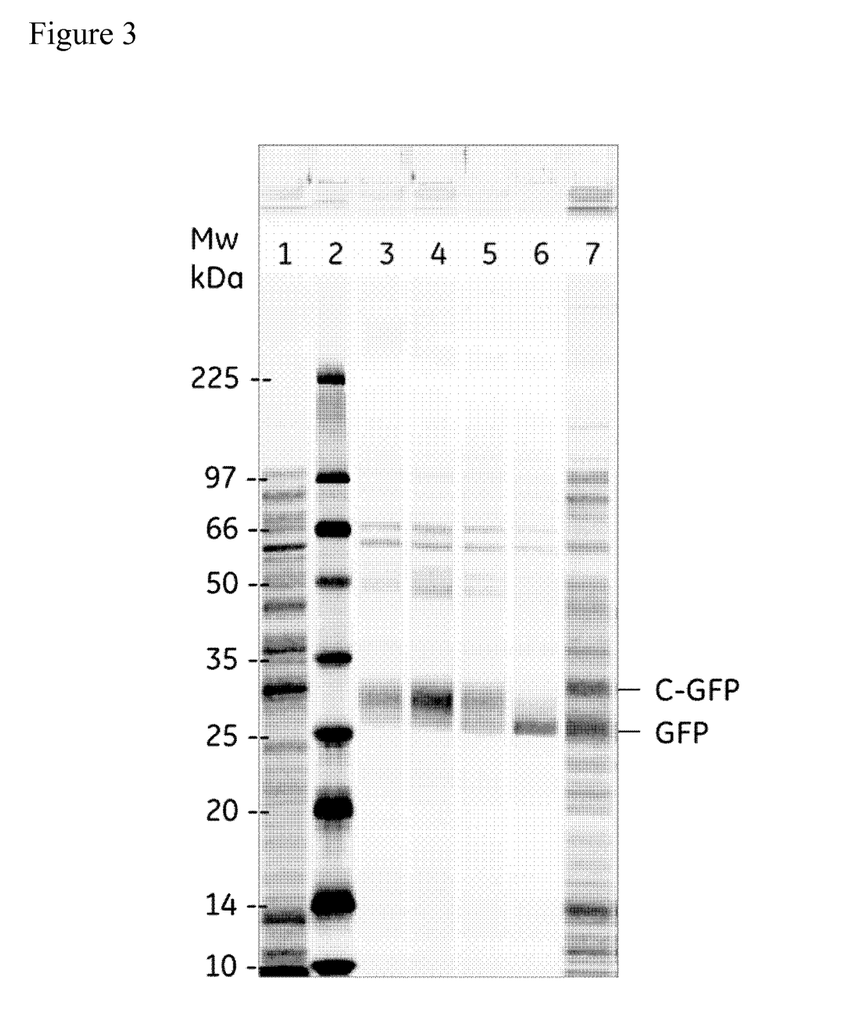
FIG. 3: SDS-PAGE analysis of fractions taken during the purification of tag-less GFP as described in FIG. 2.

Results from the purification are shown in FIGS. 2 and 3. FIG. 2 shows a complete purification cycle with first sample loading on an equilibrated affinity column, where the absorbance at 280 nm (thick solid line) show the flowthrough of non-binding proteins from the E. coli lysate. Then the washing with binding buffer until the absorbance at 280 nm is close to zero. Then the cleavage and elution is initiated by pumping the cleavage buffer onto the column followed by a pause for 30 minutes with 0 ml/min flowrate. Then the flowrate is raised to 1 ml/min until eluted material has been isolated. Finally the column is regenerated with 50 mM NaOH, 1.5 M NaCl which can be seen by a sharp rise in the conductivity, (thin dotted line) followed by washing with cleavage buffer and binding buffer.

FIG. 3 shows an SDS-PAGE analysis of fractions taken during the purification in FIG. 2. SDS-PAGE was carried out on Amersham WB system, (GE Healthcare), using gel card 14, 13.5% with Cy-5 labelling. Lane 1 show the clarified E. coli lysate containing the recombinantly expressed C-GFP, (SEQ ID no. 6), which is the starting material. Lane 2 contains a molecular size marker. Lanes 3, 4 and 5 represent the early fractions during elution when cleavage buffer is pumped onto the column. Some loosely bound C-GFP can be seen in the early fractions. Lane 6 show the eluted protein after incubation for 30 minutes consisting of GFP after cleavage from the NpuDnaE C-fragment. Lane 7 show a fraction from regeneration using 50 mM NaOH, 1.5 M NaCl. The fraction contains some uncleaved as well as cleaved test protein, (C-GFP respectively GFP) together with E. coli proteins. Fractions in the later part of the peak during elution thus contains tag-less test protein GFP and can be pooled for a subsequent polishing purification step or for other research.

The invention claimed is:

1. A method for production of an affinity chromatography resin comprising an N-terminal split intein fragment as an affinity ligand, comprising the following steps:
   a) expression of an N-terminal split intein fragment, wherein the N-terminal split intein fragment comprises a sequence selected from SEQ ID NO:s 1-5 or a sequence having at least 95% homology therewith and an Alanine at the fourth position and a Serine at the thirty-first position, as insoluble protein in inclusion bodies in bacterial cells,
   b) harvesting said inclusion bodies;
   c) solubilizing said inclusion bodies and releasing expressed protein;
   d) binding said protein on a solid support;
   e) refolding said protein;
   f) releasing said protein from the solid support; and
   g) immobilizing said protein as ligands on a chromatography resin to form an affinity chromatography resin—wherein the ligand density on said chromatography resin is 5-10 mg ligand/ml resin.

2. The method according to claim 1, wherein the N-terminal split intein fragment comprises a sequence selected from SEQ ID NO:s 1-5.

3. The method according to claim 1, wherein said chromatography resin is selected from the group consisting of agarose, polystyrene, methacrylate and cellulose beads.

4. The method according to claim 1, wherein the immobilization in step g) is by covalent attachment.

5. The method according to claim 1, wherein said immobilization is preceded by concentration to a protein concentration between 5-30 mg/ml.

6. The method according to claim 1, wherein the chromatography resin is packed in a column, fluidized bed, porous monolith or capillary bed.

7. The method according to claim 1, comprising binding of the N-terminal fragment on an ion exchange column in step d).

8. The method according to claim 1, wherein the N-terminal fragment is tagged, and the solid support in step d) is an IMAC column.

9. The method according to claim 1, wherein said chromatography resin is agarose beads.

10. The method according to claim 1, wherein the N-terminal fragment is poly-histidine tagged, and the solid support in step d) is an IMAC column.

11. The method according to claim 1, wherein the N-terminal split intein fragment a sequence having at least 95% homology to one of SEQ ID NO:s 1-5, an Alanine at the fourth position, a Serine at the thirty-first position, and a Serine at the sixty-second position.

* * * * *